United States Patent
Walther et al.

(10) Patent No.: US 9,554,873 B2
(45) Date of Patent: Jan. 31, 2017

(54) MAXILLO-MANDIBULAR FIXATION APPARATUS AND METHOD

(76) Inventors: Russell B. Walther, Gainesville, FL (US); Charles C. Hanley, Oklahoma City, OK (US)

( * ) Notice: Subject to any disclaimer, the term of this patent is extended or adjusted under 35 U.S.C. 154(b) by 1188 days.

(21) Appl. No.: 13/113,026

(22) Filed: May 20, 2011

(65) Prior Publication Data

US 2011/0288551 A1    Nov. 24, 2011

Related U.S. Application Data

(60) Provisional application No. 61/347,411, filed on May 22, 2010.

(51) Int. Cl.
*A61C 7/36* (2006.01)
*A61C 7/00* (2006.01)
*A61C 5/00* (2006.01)

(52) U.S. Cl.
CPC ........ *A61C 5/007* (2013.01); *A61C 7/36* (2013.01)

(58) Field of Classification Search
USPC .... 606/74, 139–141, 103; 433/8, 18, 19, 23, 433/24
See application file for complete search history.

(56) References Cited

U.S. PATENT DOCUMENTS

| | | | | |
|---|---|---|---|---|
| 1,638,006 A * | 8/1927 | Aderer | ............................. | 602/5 |
| 2,481,177 A * | 9/1949 | Tofflemire | ............... | A61C 7/00 433/18 |
| 2,502,902 A * | 4/1950 | Tofflemire | ...................... | 606/54 |
| 4,202,328 A * | 5/1980 | Sukkarie | ......................... | 433/18 |
| 4,364,380 A * | 12/1982 | Lewis | ...................... | A61C 7/00 132/321 |
| 4,643,178 A * | 2/1987 | Nastari et al. | .................. | 606/74 |
| 4,813,869 A * | 3/1989 | Gatewood | ....................... | 433/18 |
| 4,832,063 A * | 5/1989 | Smole | ................... | A61C 15/041 132/321 |
| 4,872,449 A | 10/1989 | Beeuwkes, III | | |
| 5,395,374 A * | 3/1995 | Miller et al. | .................... | 606/74 |
| 5,415,658 A * | 5/1995 | Kilpela et al. | ................ | 606/300 |
| 5,423,820 A * | 6/1995 | Miller et al. | .................... | 606/74 |
| 5,536,270 A * | 7/1996 | Songer et al. | .................. | 606/74 |
| 5,569,253 A * | 10/1996 | Farris et al. | ................... | 606/74 |
| 5,613,853 A * | 3/1997 | Chasan et al. | ............... | 433/215 |
| 5,772,663 A * | 6/1998 | Whiteside et al. | ............. | 606/74 |
| 5,964,765 A * | 10/1999 | Fenton et al. | ................. | 606/232 |

(Continued)

*Primary Examiner* — Zade Coley
(74) *Attorney, Agent, or Firm* — Gagnon, Peacock & Vereeke PC; Aaron P. Peacock (57) ABSTRACT

The present disclosure provides for an apparatus and method for supporting a maxillo-mandibular fixation by securing the maxillary teeth and mandibular teeth together in a faster and less harmful manner, includes a floss-wire component for circumdental wiring a tooth initially by flossing the interproximal space of a tooth therewith and thereafter causing circumdental wiring of a tooth when the floss-wire component is pulled, the floss-wire component having a distal portion composed of a floss-like material and a proximal portion composed of a wire-like material, a clip having an anchoring point and grasping point, the clip interacts with the floss-wire component, thereby causing the clip and the floss-wire to secure tightly to a tooth, and a bar positioned between the buccal surface of one or more teeth and one or more clips, the bar having a plurality of indices to increase the stabilization of one or more clips.

20 Claims, 10 Drawing Sheets

(56) References Cited

U.S. PATENT DOCUMENTS

| | | | |
|---|---|---|---|
| 6,086,590 A * | 7/2000 | Margulies et al. | 606/263 |
| 6,302,889 B1 * | 10/2001 | Keller | 606/74 |
| 6,575,741 B2 | 6/2003 | Campbell | |
| 2005/0282115 A1 | 12/2005 | Gedebou | |
| 2010/0124727 A1 * | 5/2010 | Shah et al. | 433/19 |

* cited by examiner

MAXILLO-MANDIBULAR FIXATION APPARATUS AND METHOD

CROSS-REFERENCE TO RELATED APPLICATIONS

Applicants claim priority to U.S. Provisional Patent Application No. 61/347,411, filed May 22, 2010, the disclosure of which is incorporated by reference herein in its entirety.

DETAILED DESCRIPTION

Integral to the practice of dentistry and medicine is the procedure of temporarily securing the maxilla to the mandible, thereby stabilizing the bones of the jaw to effectuate proper healing of facial fractures. Generally, medical treatments of maxillofacial injuries involve facial bone immobilization and stabilization. It is commonplace to stabilize the maxillofacial region of the upper and lower jaws utilizing a surgical procedure known as maxillo-mandibular fixation.

In a maxillo-mandibular fixation procedure, fixation, stabilization techniques involve securing the mandibular teeth and the maxillary teeth to a mandibular arch bar and maxillary arch bar respectively. After the teeth have been secured to the respective arch bars, the arch bars are secured one to another, thereby immobilizing and stabilizing the upper and lower jaws. While multiple methods of fixation, reduction and stabilization have been proposed, the mainstay of placing an individual in maxillo-mandibular fixation, or MMF, involves placing arch bars around the teeth.

An arch bar, also known as a support bar, is a single piece of flexible metal that is placed perpendicular to the long axis of the teeth and on the buccal surface of the teeth. Generally, the arch bar is cut to the appropriate length and arched in form to properly fit the contours of the dentition within the oral cavity. Once the mandibular arch bar is secured to the mandibular teeth and the maxillary arch bar is secured to the maxillary teeth, the two respective arch bars are secured together via inter-arch wiring. The upper and lower jaws are drawn together by tightening inter-arch wires that are looped around the respective arch bars. The inter-arch wiring forces the teeth into occlusion, providing stable fixation of the jaws.

The mandibular and maxillary arch bars are secured to a plurality of individual mandibular and maxillary teeth, respectively. For example, a plurality of the manibular teeth are each individually secured to the manibular arch bar. To secure each individual tooth to the respective arch bar, a conventional procedure known as circumdental wiring is employed. Circumdental wiring involves the passing of one end of flexible wire through the interproximal space located on a side of a tooth near the gingiva, around the tooth's lingual surface, through the interproximal space located on the tooth's other side, and around the arch bar positioned on the tooth's buccal surface. As the wire is passed through the various sections, it is bent to the appropriate shape. After the wire has been passed through the various sections, it is tightened so that it substantially conforms to the contours of the tooth. Then, the two ends of the wire are twisted together, thereby holding the arch bar against the tooth. This process is repeated for each individual tooth to firmly secure the respective arch bar. Once each respective arch bar is stabilized, maxillo-mandibular fixation can be established by wiring the mandibular and maxillary arch bars together.

While the conventional practice of circumdental wiring of teeth is common among surgeons during maxillo-mandibular fixation procedures, it has many drawbacks and disadvantages. For example, the practice can be quite time-consuming to perform. Because a plurality, if not all, of the teeth located on the maxillary and mandible are secured to the appropriate arch bar, circumdental wiring of each tooth must be accomplished. Circumdental wiring of one tooth can be a tedious undertaking that expends time for the surgeon as he or she must insert the wire in the interproximal space of a side of the tooth, bend the wire around the tooth, find and insert the wire into the interproximal space of the other side of the tooth usually using fingers, and then utilize a tool such as forceps pliers to twist the two ends of the wire together. When a surgeon performs this practice multiple times for multiple teeth on a patient, much time is expended.

Additionally, because of the small diameter of the wire that is used during the practice of circumdental wiring, both the surgeon and the patient are placed at risk of occupational exposure due to glove perforation. The wire can easily puncture the surgeon's glove as the professional manipulates the wire to conform to the contours of a tooth and twists the end of the wire to secure the appropriate arch bar to the tooth. The professional's fingers are likely to be pierced and/or cut by an end of the wire during the practice, thereby exposing both the professional and patient to a potentially harmful situation.

Furthermore, because of the small diameter of the wire, the wire is prone to breaking during manipulation. If the wire breaks while circumdental wiring a tooth, the broken wire along with any broken pieces may need to be removed from the mouth. Then, a new wire may need to be used, requiring the surgeon to begin the circumdental wiring of that particular tooth anew. This not only increases the time expended during the maxillo-mandibular fixation procedure but also increases the physical danger to both dental professional and patient alike.

Also during the circumdental wiring practice, the wire often penetrates the interdental gingiva of a patient as the wire is passed the tooth. This causes unnecessary damage to gum tissue and may cause significant patient bleeding and pain. Other times during the circumdental wiring practice, the wire is deflected and does not pass through the occluded gingival embrasures due to calculus or other foreign bodies present in and around the area. This causes the wire to deform and deflect. As such, the shape of the wire must be adjusted and corrected, which may impact the tensile strength of the wire as well as consume more time and energy during the maxillo-mandibular procedure.

Therefore, it is evident that current and customary maxillo-mandibular systems, procedures and processes are inefficient and wrought with problems. Embodiments of the present invention of a bar and clip system and process disclosed herein provide for an increase in the efficiency, safety and efficacy of the practice and procedure of maxillo-mandibular fixation. As a result, a surgeon, utilizing the embodiments of the bar and clip system and process, can more quickly place a patient in maxillo-mandibular fixation while reducing the risk of injury to both dental professional and patient alike. Furthermore, the present invention provides a patient a more comfortable experience.

The present invention comprises many different embodiments. One embodiment includes a bar that extends along the arch of either the maxillary teeth or mandibular teeth, a clip which aids in securing the bar to a particular tooth, and a floss-wire component which secures and anchors the clip and bar to the tooth. The floss-wire component may be incorporated into the clip, so that it is inseparable therefrom; also, the floss-wire component may be a stand-alone component that integrates with the clip. The clip may be constructed to include a grasping mechanism therein that grasps the floss-wire component during the circumdental process, or it may be constructed to include a finger that protrudes therefrom, such that once the floss-wire component is inserted therein and the finger is crimped, the floss-wire component is grasped by the finger. As is evident from the above, many different embodiments of the present invention can be constructed.

A feature and advantage of the embodiments of the present invention involves the streamlining of the practice of circumdental wiring a tooth during maxillo-mandibular fixation. Instead of the customary practice of inserting an end of a wire into the interproximal space of the side of a tooth, passing the wire therethrough, bending the wire around the tooth's lingual surface, inserting the end of the wire through the interproximal space of the tooth's other side, passing the wire therethrough, and then twisting the two ends of the wire together to aid in holding an arch bar in place, a floss-wire component, having a floss-like material attached at one end and a wire-like material connected to the other end, is utilized initially to more easily substantially circumvent the tooth. At the outset, the tooth is flossed with floss-like material, utilizing techniques similar to those utilized when flossing between teeth. As such, the elongated portion of the floss-like material is inserted into a tooth's occlusal embrasure and passed into the tooth's interproximal space in the same manner as if the tooth was being flossed. Then, the floss-like material is directed and passed around the tooth's lingual surface. After that, the floss-like material is inserted into occlusal embrasure located on the tooth's other side and passed into the tooth's interproximal space. Then, the floss-like material is pulled, thereby causing the wire-like material to pass around and circumvent the tooth. Because the wire-like material is guided into position substantially around the tooth by the floss-like material, a surgeon's customary practice of manipulating a wire during the circumdental wiring process is minimized, thereby speeding up the process while also increasing the safety of patient and surgeon alike.

The clip aids in securing the bar to the buccal surface of a tooth. The clip may include an anchoring point and may also include a grasping point. The anchoring point and grasping point of the clip interact with the floss-wire component to secure the clip and bar to the tooth. In one embodiment, the floss-wire component is fed from the anchoring point of the clip, flossed around the tooth, pulled to cause circumdental wiring of the tooth, fed into the grasping point, and then grasped by the grasping mechanism. In another embodiment, the floss-wire component is fed into a finger that protrudes from the clip, and the finger and floss-wire component therein are crimped, thereby effectuating the grasping result.

The bar, similar to an arch bar, engages the clip and contacts the surface of a tooth. The bar may include indices which allow it to more properly engage the clip. The indices prevent the bar from shifting after the bar is secured to the clip and the tooth. Additionally, the bar may engage many teeth at once. After a bar is secured to the maxillary teeth and a bar is secured to the mandibular teeth, the two bars can be interconnected to accomplish maxillo-mandibular fixation.

Of the many features and advantages of the embodiments of the present invention, one includes the new and innovative technique and process to circumdental wire a tooth as briefly discussed above. Because of the new technique, circumdental wiring a tooth can be performed with increased speed. Also, both surgeon and patient are less prone to being pricked by a wire. This is because each tooth is flossed with the floss-wire component first and then the wire-like material is positioned around the tooth via the floss-like material connected to the floss-wire component. Thus, the dental professional does not attempt to insert a wire through the interproximal space between the teeth as is the current and customary practice and procedure in the industry. As a result, risk of damage to a patient's gingiva is decreased. Also, the dental professional is less likely to be punctured by the end of a wire during the procedure, thereby decreasing the risk of occupational exposure due to glove perforation. Furthermore, wire deformation due to calculus or plaque is also decreased.

Moreover, the indices positioned on the bar keep the bar from sliding or moving after it has become secured to the teeth. Due to the indices, forces are more accurately transferred from the floss-wire component, clip, and tooth to the bar. More accurate transfer of forces provides a better level of comfort for the patient as well as a more effective means of accomplishing maxillo-mandibular fixation.

Figure 1:
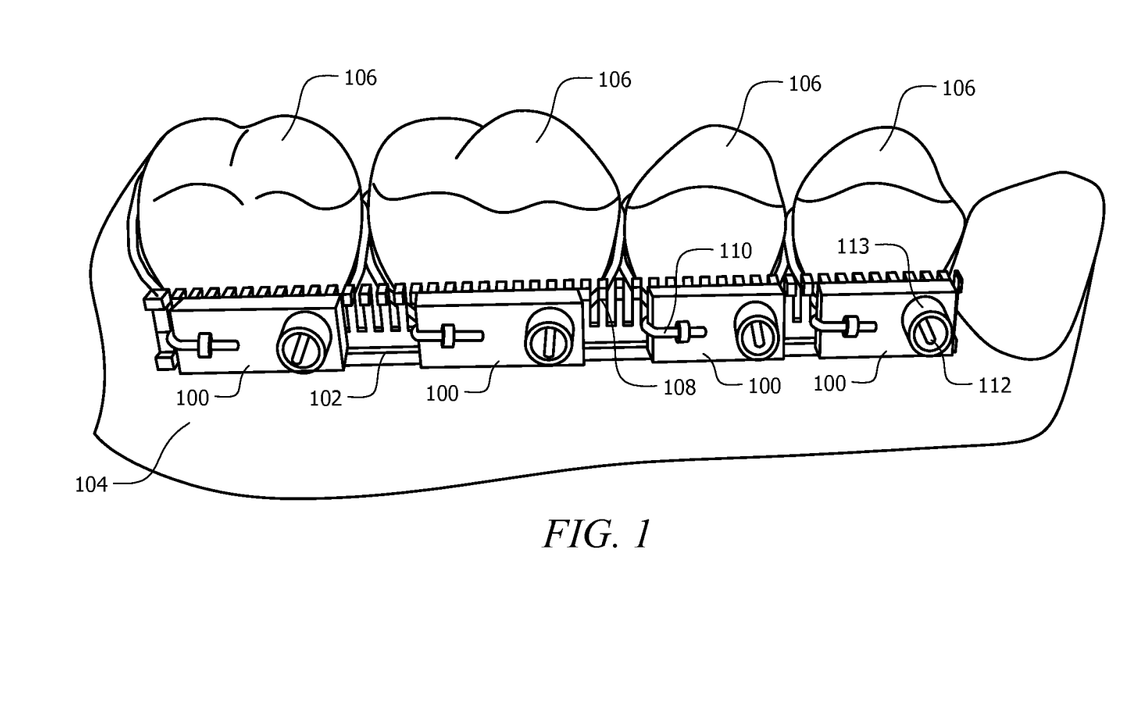
FIG. 1 is a perspective view of a segmental arch bar securing the buccal surface of a plurality of teeth and engaging a plurality of clips utilizing the wire-like material of a floss-wire component comprising an embodiment of the present invention.

For a better understanding of some of the many embodiments of the present invention, drawings are included herewith. In FIG. 1 of the drawings, an embodiment of the present invention is illustrated. In FIG. 1, several clips 100 are shown engaging a bar 102. The bar 102 extends along the buccal surface 104 of a plurality of teeth 106. The bar 102 has a plurality of indices 108 to engage the wire-like material 110 that substantially wraps around each tooth 106, a practice known as circumdental wiring. Each clip 100 engages the bar 102 and aids in securing the bar 102 to each tooth 106. As shown in FIG. 1, an end 112 of the wire-like material 110 has been cut. The end 112 can be cut utilizing methods and/or devices that are currently known in this art to cut wire and wire-like material 110, such as but not limited to pliers, pliers-like devices, or bending the wire-like material 110 manually to cause breaking, etc. The end 112 is cut after the bar 102 has been tightly secured to the tooth 106.

FIG. 1 depicts an embodiment of the present invention applied to a plurality of teeth 106. It should be noted that the bar 102 may be an arch bar and may arch the entire length of teeth located on the maxilla or mandible. Also, the bar 102 may be customized in length to the dimensions of a particular patient's arch. After the dental professional has determined the length of a patient's arch, the bar 102 may be customized in length and cut with pliers or a pliers-like device to the appropriate length for the particular patient.

Also, FIG. 1 depicts a finger 113 protruding from each clip 100. A finger 113 or other protrusion jutting out from the clip 100 can be used to interconnect a bar that is secured to maxillary teeth to a bar that is secured to mandibular teeth, thereby causing maxillo-mandibular fixation. For example, an inter-arch anchoring lug may be present, attached to a clip that is secured to teeth located on the mandible and attached to a clip that is secured to teeth on the maxilla. However, other embodiments are envisioned such that a clip 100 can function also as a lug wherein inter-arch wiring is passed completely around the clip 100 in its entirety, thereby causing the clip 100 to also function as an inter-arch anchoring lug.

Figure 2:
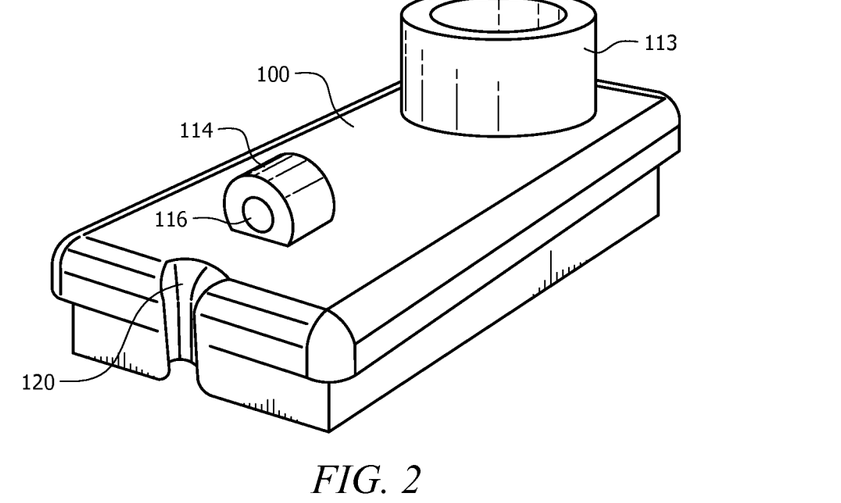
FIG. 2 is a perspective view of the clip as shown in FIG. 1.

FIG. 2 depicts a clip 100. The clip 100 comprises an anchoring point 114 and a grasping point. The anchoring point 114 juts out of the front portion of the clip 100 and is defined by an aperture 116. The aperture 116 integrates with a floss-wire component and allows the floss-wire component to move therethrough. Other embodiments are envisioned incorporating the floss-wire component within the anchoring point 114 of the clip 100. Therefore, the floss-wire component would form part of and would be attached to the clip 100.

Also in FIG. 2, a finger 113 protrudes from the clip 110. The finger 113 can house a grasping mechanism within the grasping point of clip 100. The grasping mechanism grasps the wire-like material 110 of the floss-wire component. Alternatively, the finger 113 can be crimped once the wire-like material 110 is passed through the grasping point and into the finger 113, thereby effectuating a grasp of the wire-like material 110. As mentioned above, the finger 113 can also be utilized to interconnect a maxillary bar and a mandibular bar, thereby causing maxillo-mandibular fixation.

The clip 100 may also include a channel 120 to provide a pathway for the floss-wire component as the floss-wire component passes through the anchoring point 114, bends around the side surface of the clip 100 and passes substantially around a tooth. The channel 120 provides a restricted passageway that provides control during the anchoring process, thereby increasing the likelihood that the clip 100 will aid in securing the bar 102 at an appropriate position and angle. Accordingly, the channel 120 ensure that the clip 100 contacts the bar 102 evenly, such that every square inch of the clip 100 applies substantially the same force to the bar 102 when it is secured thereto.

Figure 3:
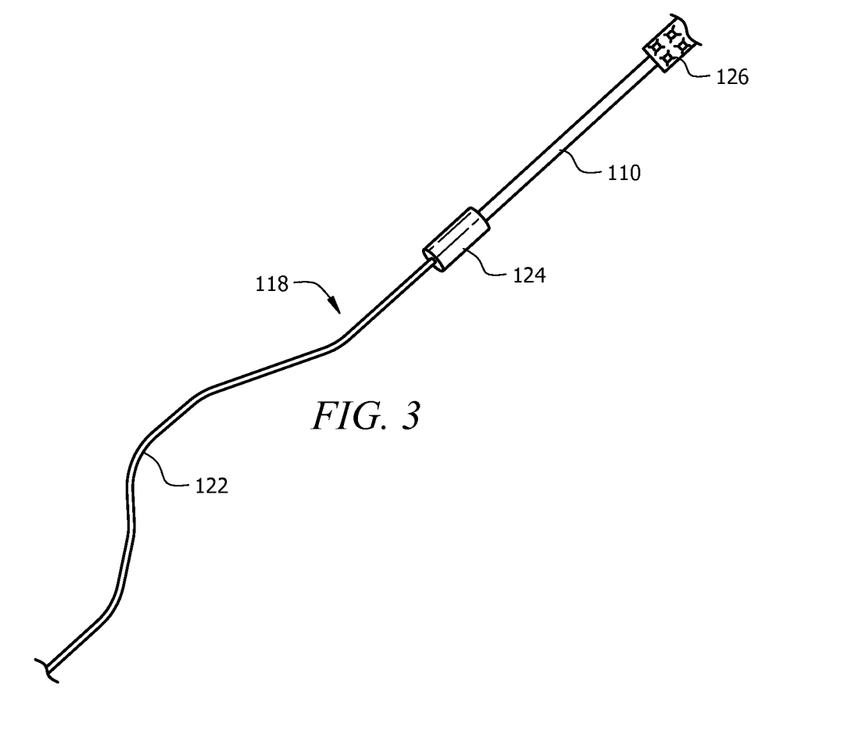
FIG. 3 is a perspective view of a floss-wire component.

FIG. 3 depicts a floss-wire component 118. The floss-wire component 118 is divided into two portions: a floss-like material 122 and a wire-like material 110. The floss-like material 122 and the wire-like material 110 are joined together via a floss-wires junction 124. Persons of ordinary skill in this art will appreciate that the floss-wire junction 124 can join together the floss-like material 122 and the wire-like material 110 in any manner. For example, the two portions can be glued together, fastened together, bonded together, knotted together, tied together, hooked together, etc. Also, the floss-wire junction 124 can house an apparatus that joins the two portions together.

In the embodiment depicted in FIG. 3, the end portion 126 of the wire-like material 110 has been crimped. The crimping of the end portion 126 of the wire-like material 110 will impede the end portion 126 from passing through the anchoring point 114, thereby causing the wire-like material 110 to append to the anchoring point 114.

The floss-like material 122 can be comprised of any flexible elongated strip of material having adequate strength when wet to resist breaking when pulled back and forth in an interproximal space between teeth and sufficiently soft when wet to avoid piercing gum tissue. As such, the floss-like material 122 may comprise a regular everyday type of dental floss such as but not limited to polytetrafluoethylene or string form. Furthermore, the floss-like material 122 may comprise of but not limited to nylon, multifilament or monofilament floss. Additionally, the floss-like material may be waxed or unwaxed.

The wire-like material 110 can be comprised of regular everyday type of dental wire that is commonly used in the field of dentistry such as but not limited to 316L stainless steel, metal, plastic, polymer, etc. Furthermore, the wire-like material 110 may be comprised of monofilament or multifilament material.

Figure 4:
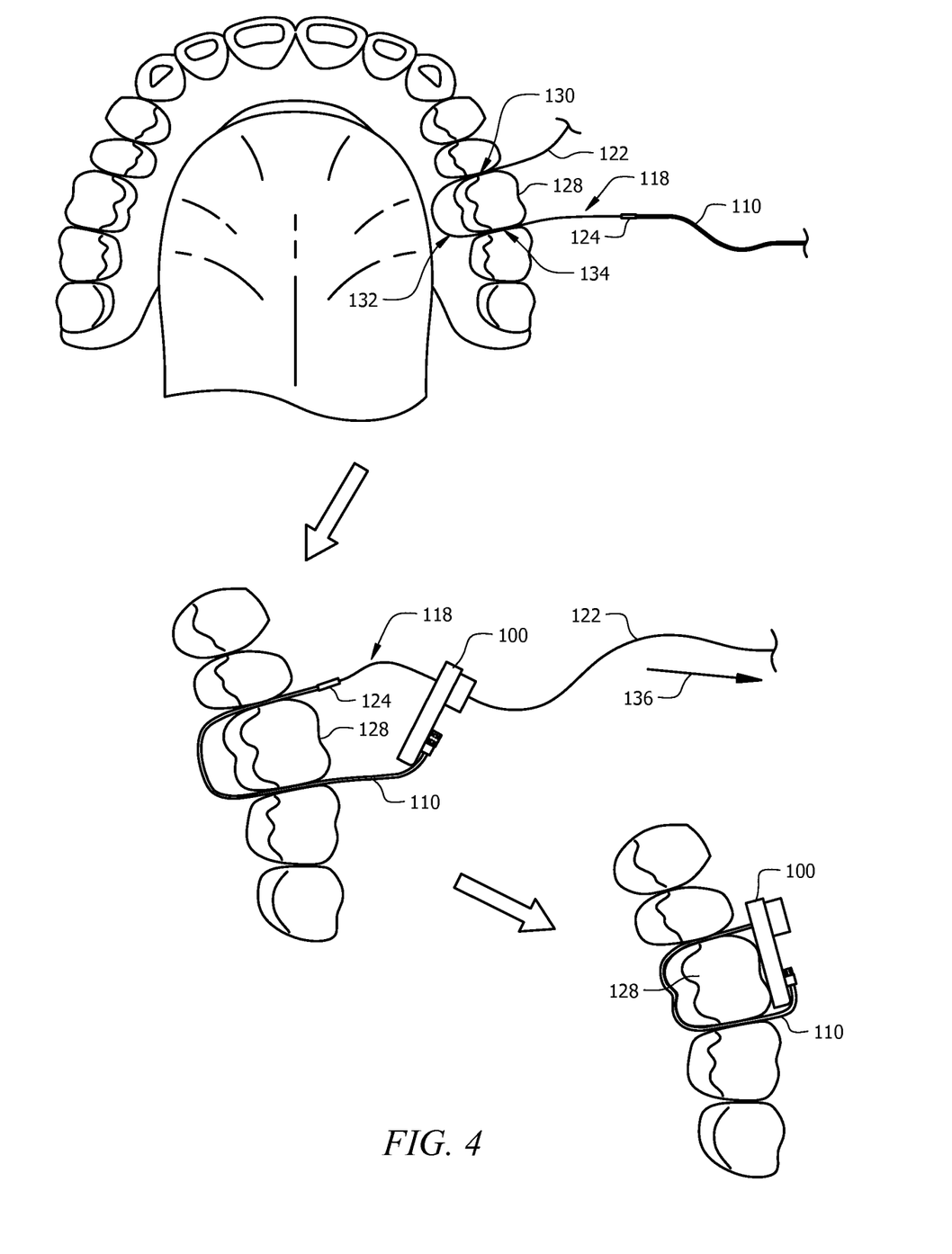
FIG. 4 is a top view of a method of circumdental wiring a tooth utilizing the floss-wire component and the clip of FIGS. 1 and 2.

FIG. 4 depicts the process and procedure of circumdental wiring a tooth utilizing the floss-wire component 118 in conjunction with the clip 100. For clarity's sake, the bar 102 is not depicted, though in practice, the bar 102 would be positioned between the buccal surface of the teeth and the clip 100 during this process and procedure. Initially, a tooth 128 is flossed with the floss-like material 122 of the floss-wire component 118, utilizing techniques similar to those used when flossing teeth. As such, the longitudinal portion of the floss-like material 122 is inserted into the occlusal embrasure 130 of the tooth 128 and further inserted into the tooth's interproximal space in the same manner as if the tooth 128 was being flossed. Then, the floss-like material 122 is directed and passed around 132 the lingual surface of the tooth 128. After that, the floss-like material 122 is inserted into occlusal embrasure 134 located on the other side of the tooth 128 and then further inserted into the interproximal space of the tooth 128. Subsequently, the end of the floss-like material 122 is inserted into the grasping point of the clip 100.

However it should be noted that that the floss-like material 122 can occupy the area within the grasping point of the clip 100 before this process of flossing between to the teeth begins. Furthermore, the floss-wire component 118 is adequate in length to substantially circumvent the tooth during this process. The floss-like material 122 would protrude from the finger 113 of the clip 100 so that it can be easily pulled therefrom. Therefore in practice, the clip 100 would engage a bar 102 positioned on the buccal surface of a tooth, and then the tooth would be flossed as described above. This eliminates the step of inserting the floss-like material into the grasping point of the clip 100.

The floss-like material 122 is then pulled through the grasping point and finger 113 of the clip 100 and in the direction of the arrow 136, thereby causing the wire-like material 110 to pass around and circumvent the tooth 128. Finally, the floss-wire junction 124 passes through the grasping point and finger 113 of the clip 100. At that point, the grasping mechanism of the clip 100 grasps the wire-like material 110, securing the clip 100 to the tooth 128. Then, pliers or a similar device can be used to trim the excess wire-like material 110 protruding from the finger 113.

Figure 5:
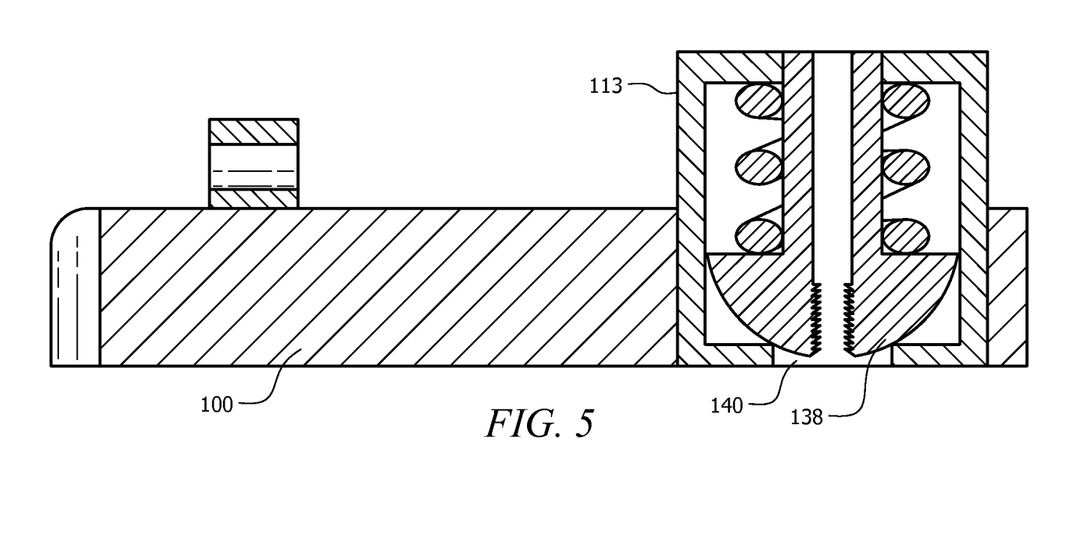
FIG. 5 is a top view of a clip having a grasping mechanism comprising an embodiment of the present invention.

FIG. 5 depicts an embodiment of the clip 100 having a grasping mechanism 138 housed within the grasping point 140 and finger 113. Once the wire-like material 110 enters the grasping point 140 and the grasping mechanism 138, force is applied to the wire-like material 110, preventing the wire-like material 110 from retreating by sliding backward. The grasping mechanism 138 has the ability to apply no force, constant force, or variable force to the wire-like material 110.

Figure 6:
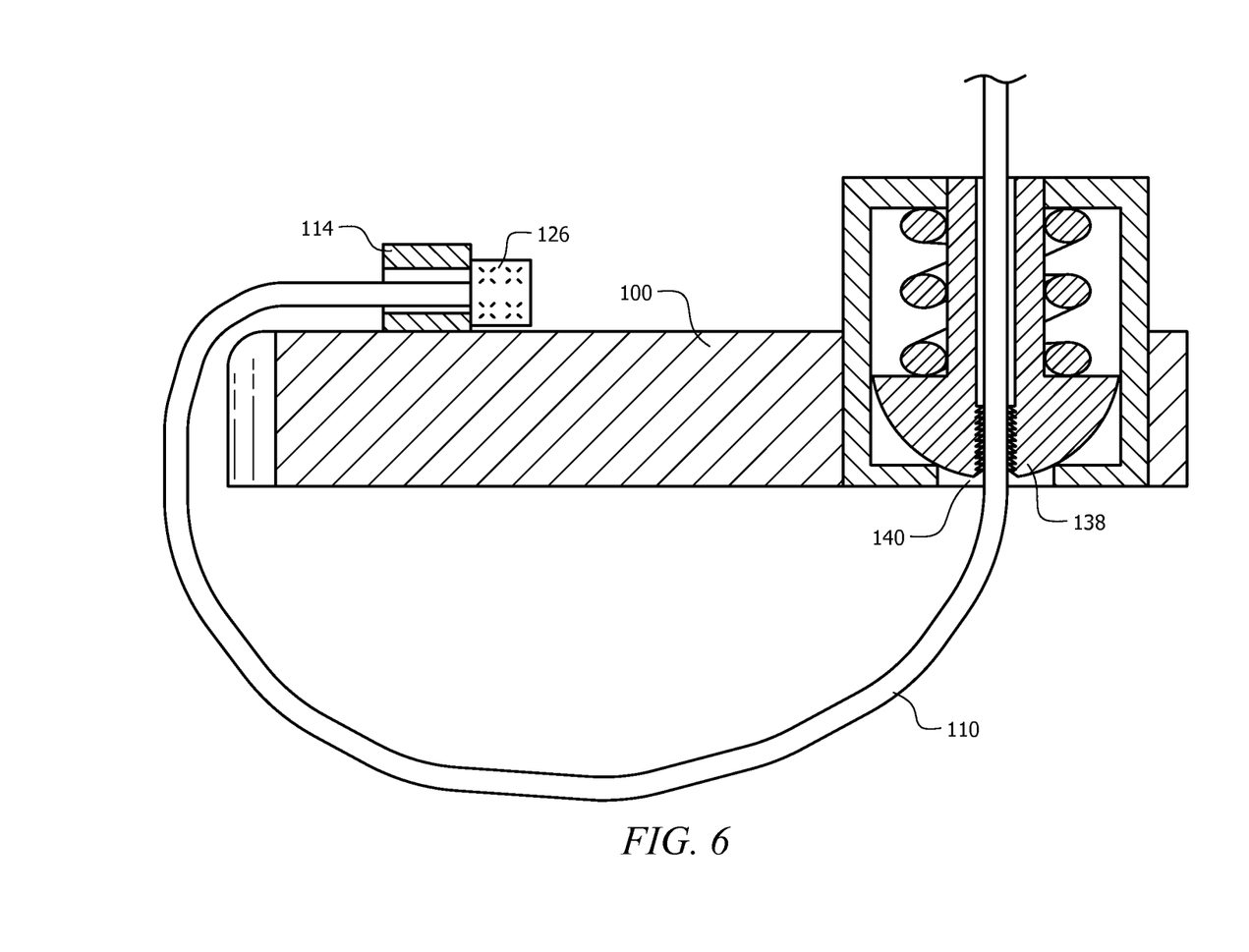
FIG. 6 is a top view of a clip having a grasping mechanism wherein wire-like material is being grasped by the grasping mechanism on one side of the clip and is being anchored on the other side of the clip by the anchoring point such that the clip and the wire-like material form a closed loop.

FIG. 6 depicts a grasping mechanism 138 within a clip 100 grasping a wire-like material 110 that was inserted into the grasping point 140. The wire-like material 110 is also anchored to the anchoring point 114 of the clip 100. The end 126 of the wire-like material 110 has been crimped to impede the end 126 from passing through the anchoring point 114. As a result, the orientation of the body of the clip 100 and the wire-like material 110 form a closed loop.

Figure 7:
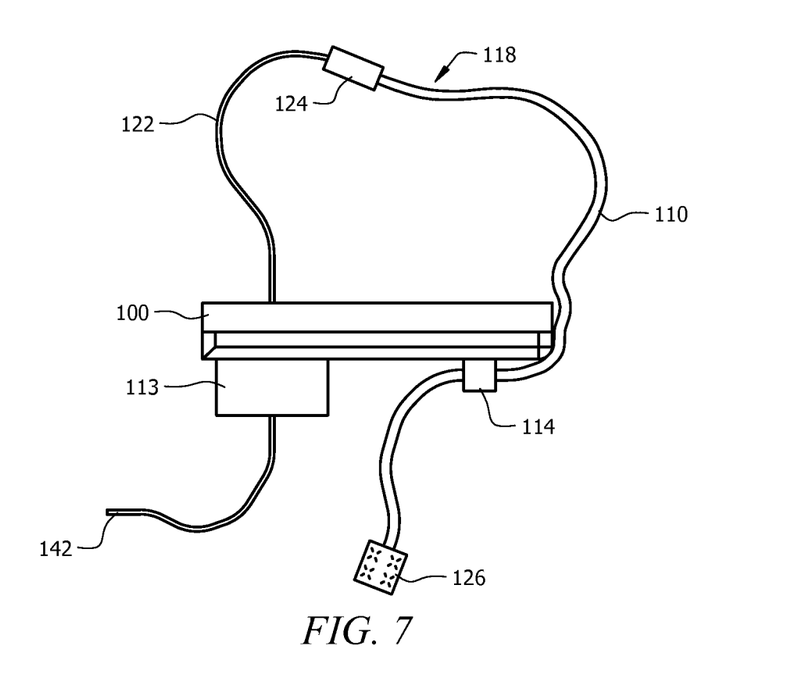
FIG. 7 is a top view of a clip interacting with the floss-wire component.

FIG. 7 depicts the floss-wire component 118 interacting with the clip 100. The floss-like material 122 and the floss-wire junction 124 of the floss-wire component 118 pass through the anchoring point 114 of the clip 100 until the clamped end 126 of the wire-like material 110 is impeded by the anchoring point 114. This results because the crimped end 126 of the wire-like material 110 is larger than the aperture 116 of the anchoring point 114. Thus, the crimped end 126 does not fit through the aperture 116 and is therefore impeded. The end 142 of the floss-like material 122 is inserted into the grasping point 140 of the clip 100 and, as depicted in this figure, through the finger 113. After passing through the grasping point 140 and finger 113, the floss-like material 122 is pulled, causing all of the floss-like material 110, the floss-wire junction 124 and a portion of the wire-like material 110 to pass through the grasping point 140.

Figure 8:
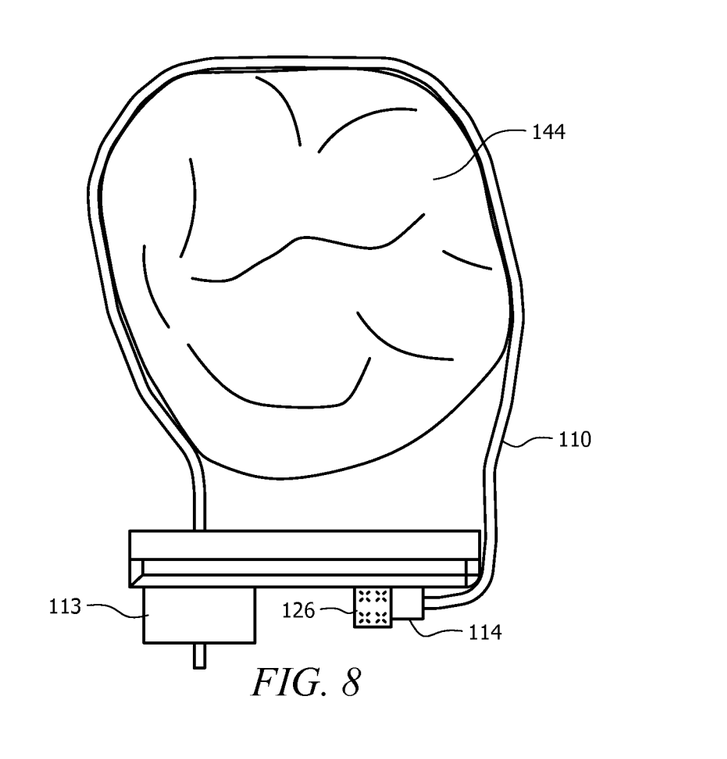
FIG. 8 is a top view of the clip in FIG. 7 wherein the grasping mechanism of the clip is grasping the wire-like material and the anchoring point of the clip is anchoring the wire-like material to the clip, thereby causing the clip to remain substantially secure to a tooth after the process of circumdental wiring the tooth.

FIG. 8 illustrates FIG. 7 after having the wire-like material 110 pulled until the crimped end 126 of the wire-like material 110 abuts the anchoring point 114. In so doing, the wire-like material 110 has substantially wrapped around tooth 144, thereby circumdental wiring the tooth 144. Furthermore, the grasping mechanism 138 maintains the force of the wire-like material 110, preventing the wire-like material 110 from retreating backward. In FIG. 8, the bar 102 is not depicted interacting with the clip 100 in the illustration as the clip 100 is only loosely secured to the tooth. Additionally as depicted in FIG. 8, only a small portion of the wire-like material 110 is protruding from the finger 113 because the remaining portion has been cut.

Figure 9A:
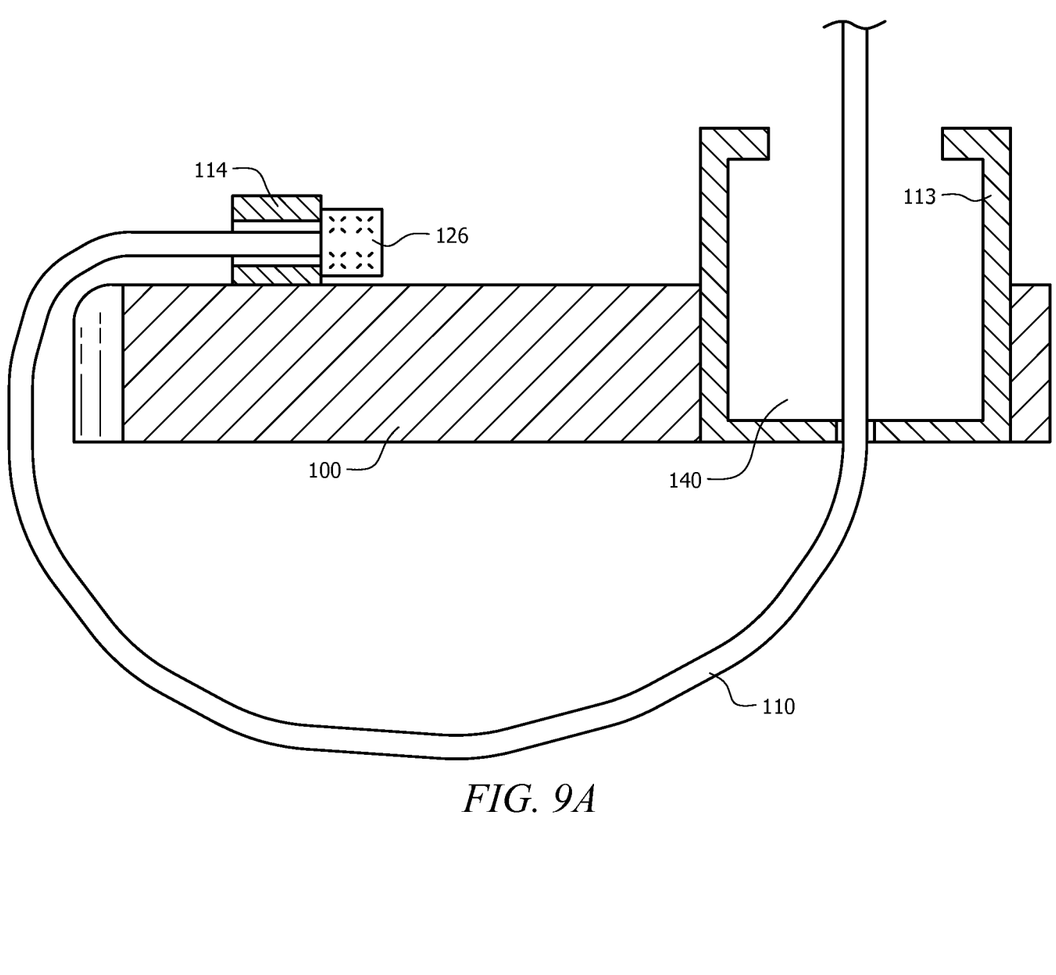
FIG. 9A is a top view of a clip interacting with wire-like material wherein the clip comprises a grasping point and finger but no grasping mechanism comprising an embodiment of the present invention.

FIG. 9A depicts another embodiment of a clip 100. In this embodiment, the grasping point 140 does not house a grasping mechanism. Instead, the floss-wire component 118 is fed through the grasping point 140 and into the finger 113. After the floss-like material 110, the floss-wire junction 124 and a portion of the wire-like material 110 have pass through the grasping point 140 such that the wire-like material 110 is tight around the tooth and the crimped end 126 of the wire-like material 110 abuts the anchoring point 114, the finger 113 is crimped using a crimping device.

Figure 9B:
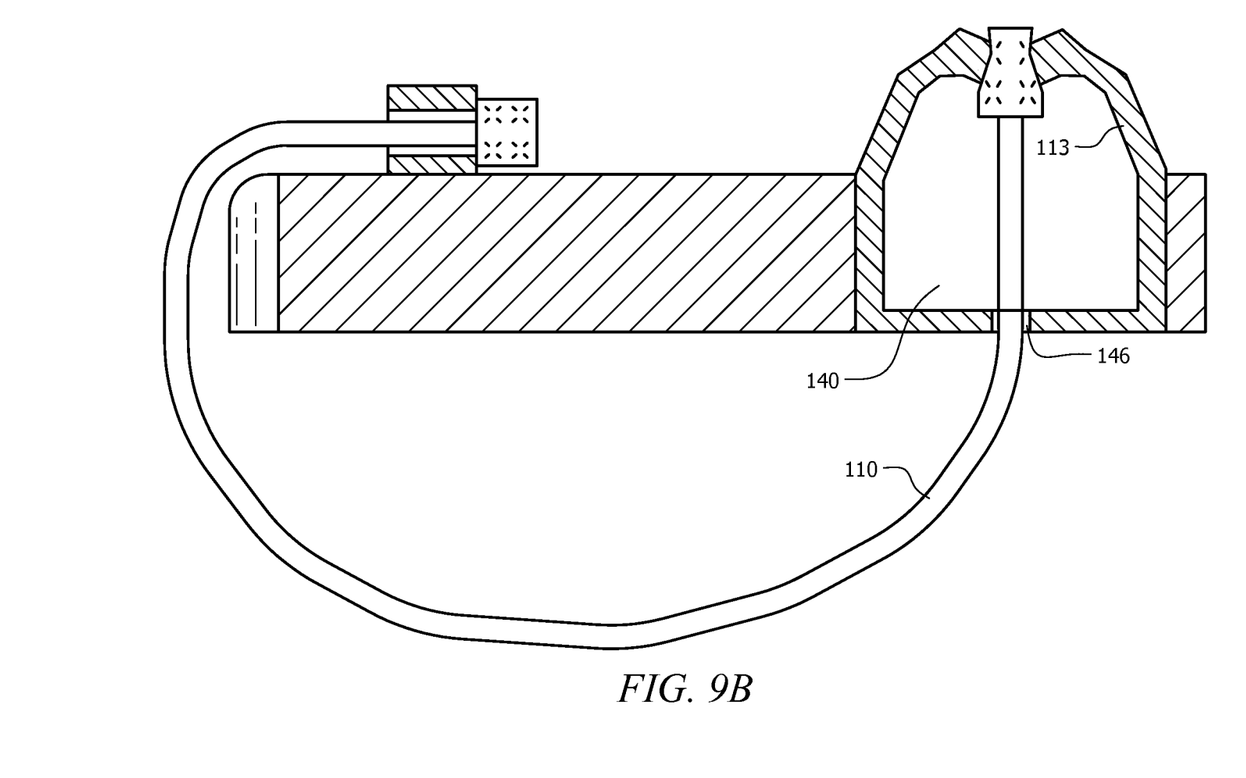
FIG. 9B is a top view of the clip in FIG. 9A wherein the wire-like material positioned within the finger are crimped, causing the finger of the clip to grasp the wire-like material.

FIG. 9B depicts the crimping of the finger 113. By crimping the finger 113, the wire-like material 110 is also crimped and becomes slightly deformed within the finger 113. Therefore, the wire-like material 110 is unable to pass backward through the aperture 146 of the grasping point 140.

Figure 10:
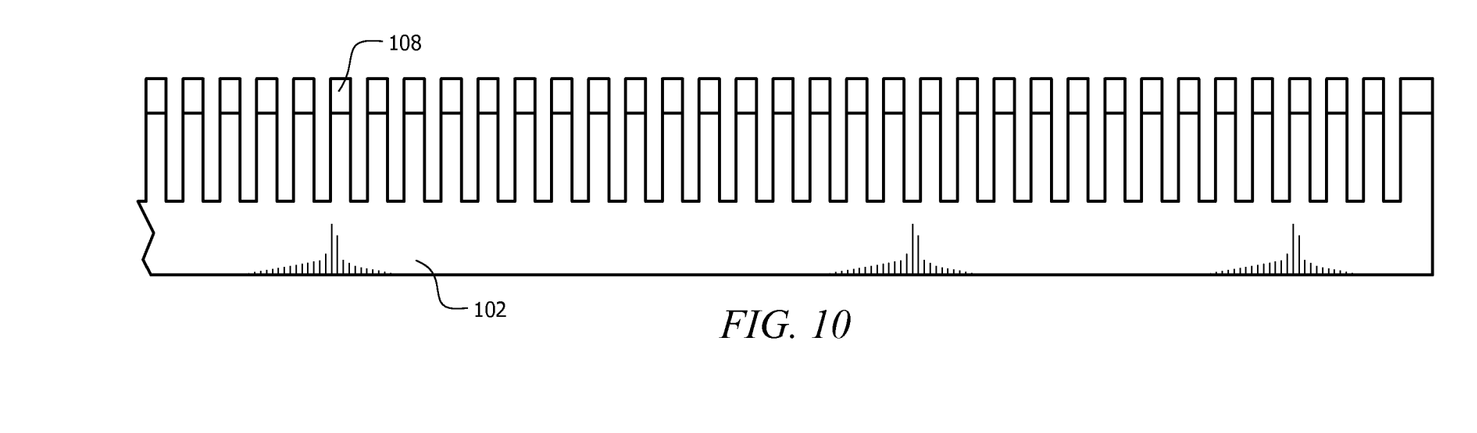
FIG. 10 is a side view of a bar.

FIG. 10 depicts the bar 102 having a plurality of predefined indices 108. The bar 102 is placed in the same orientation as a normal arch bar during maxillo-mandibular fixation—perpendicular to the long axis of the teeth on the buccal surface of the teeth. One bar 102 would be secured to the maxillary teeth and another bar 102 would be secured to the mandibular teeth. Also in further embodiments, the bar 102 can have one or more fingers protruding therefrom, thereby allowing interconnecting between a bar located on the maxillary teeth and a bar located on the mandibular teeth using inter-arch anchoring lugs.

Figure 11:
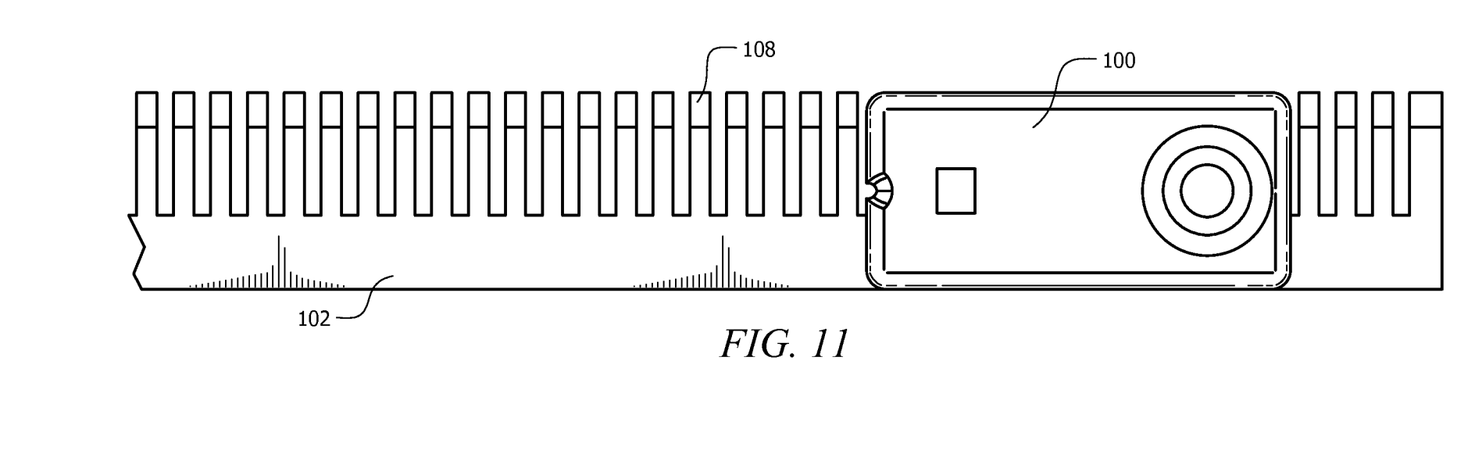
FIG. 11 is a side view of a bar interacting with a clip.

FIG. 11 depicts the bar 102 of FIG. 10 interacting with a clip 100. The body of the clip 100 is indexed on one or more sides to closely approximate the bar 102. The indexing prevents the clip 100 from moving on, across, or away from the bar 102. The indexing also serves to transfer stabilizing forces from the clip 100 to the bar 102. As illustrated in FIG. 11, the clip 100 contacts the bar 102. For clarity's sake, the floss-wire component 118 is not depicted in this figure. However the floss-wire component 118 would secure the clip 100 and bar 102 to a tooth. Because of the many indices 108 on the bar 102, the clip 100 can be positioned correctly in front of the bar 102 and tooth. Additionally, the indices will maintain the clip 100 and bar 102 in the correct position after both have been secured around a tooth via the floss-wire component 118.

Figure 12:
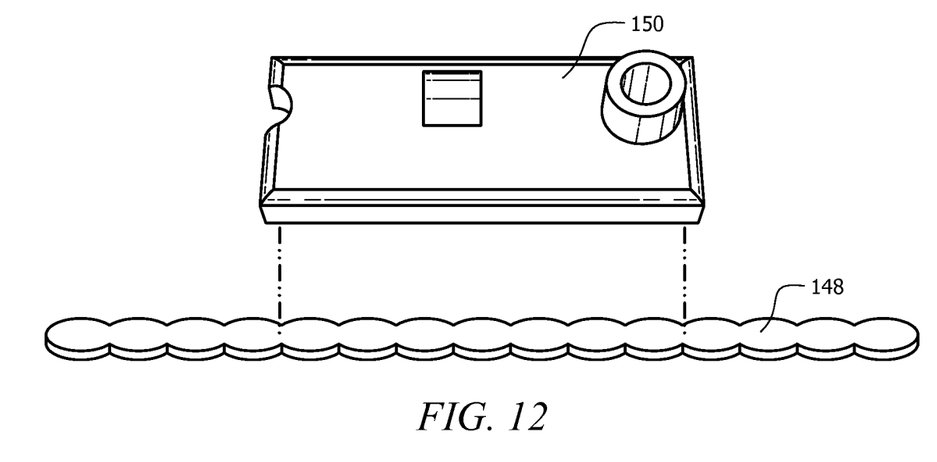
FIG. 12 is a exploded view of a clip that slidably engages a bar.
Figure 13:
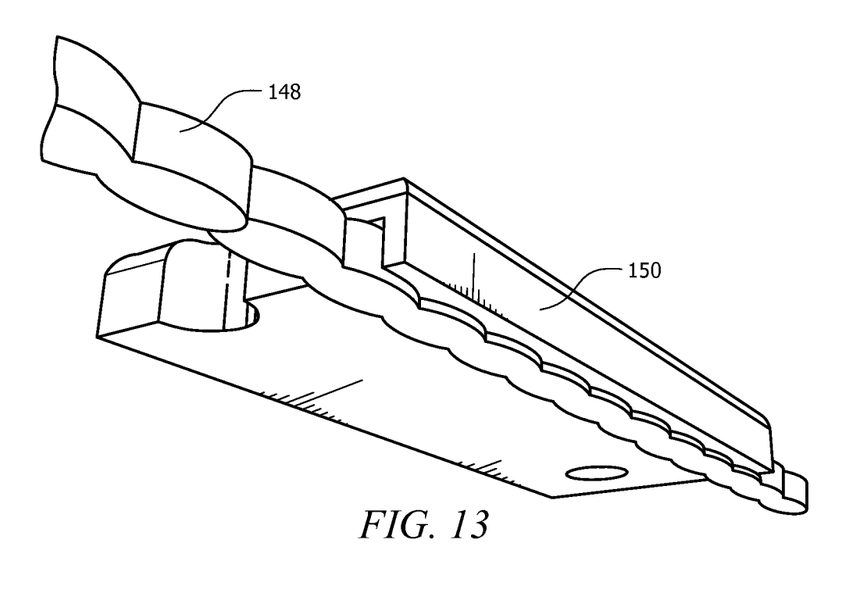
FIG. 13 is a perspective view of the clip and bar in FIG. 12 slidably engaging with each other.

FIGS. 12 and 13 depict further embodiments of the present invention. FIG. 12 depicts a bar 148 having curved indices and a clip 150. FIG. 13 illustrates how the bar 148 fits into and integrates with a clip 150. Because of the shape of the bar 148, the composition of the indices thereon, and the integration and incorporation of the bar 148 and clip 150, greater stability is gained.

Several novel methods can be employed when utilizing the many embodiments of the present invention. For example, the floss-like material 122 of the floss-wire component 118 can be inserted into the anchoring point 114 of the clip 100. Additionally, the end portion 126 of the wire-like material 110 of the floss-wire component 118 can be crimped to prevent the end portion 126 from passing through the anchoring point 114. Moreover, the floss-like material 122 of the floss-wire component 118 can be inserted into the grasping point 140 of the clip 100 until the floss-like material 122 protrudes from the finger 113 of the clip 100. These above-mentioned steps can be performed in any order.

After the three steps provided above have been performed, the clip 100 can be engaged with the bar 102. It should be noted that this step is not essential to the method of utilizing the many embodiments of the present invention but may be included.

After the steps as provided in paragraph 0053 have been performed whether including or excluding the step provided in paragraph 0054, then the following three additional steps should be performed in the sequential order provided. First, the floss-like material 122 of the floss-wire component 118 is flossed in the interproximal space between a first side of a tooth. Then, the floss-like material is directed around the lingual side of the tooth. Finally, the floss-like material 122 of the floss-wire component 118 is flossed in the interproximal space between a second side of the tooth.

After the steps provided in paragraph 0055 have been performed, the following two steps should be performed in the sequential order provided. The floss-like material 122 can be pulled until the wire-like material 110 substantially circumvents the tooth and protrudes from the finger 113 of the clip 100. Finally, the floss-like material 122 can continued to be pulled until the wire-like material 110 tightly secures substantially around the tooth.

The embodiments of the present invention apply to floss-wire components, regardless of type, function, or properties, floss-like materials, regardless of type, function or properties, wire-like materials, regardless of type, function or properties, clips, regardless of type, function or properties, bars, regardless of type, function or properties, and grasping mechanisms, regardless or type, function or properties. FIGS. 12 and 13 depict further embodiments of the present invention.

Although the many embodiments of the invention have been illustrated in the accompanying Drawings and described in the foregoing Detailed Description, it should be understood that the present invention is not limited to the embodiments disclosed, but is capable of numerous rearrangements, modifications, and substitutions of parts and elements without departing from the spirit of the invention.

What is claimed is:

1. An apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures, the apparatus comprising:
    a floss-wire component for circumdental wiring a tooth initially by flossing the interproximal space of a tooth therewith and thereafter causing circumdental wiring of a tooth when the floss-wire component is pulled, the floss-wire component having a distal portion composed of a floss-like material and a proximal portion composed of a wire-like material wherein the floss-like material and the wire-like material join together at a floss-wire junction;
    a clip having an anchoring point that anchors the wire-like material of the floss-wire component thereto and having a grasping point that grasps the wire-like material of the floss-wire component thereto, the clip interacts with the floss-wire component, thereby causing the clip and the floss-wire to secure tightly to a tooth; and
    a bar positioned between the buccal surface of one or more teeth and one or more clips, the bar having a plurality of indices to increase the stabilization of one or more clips, the bar interacts with the clip and the floss-wire component, thereby securing to a tooth.

2. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 1 further comprising a grasping mechanism within the grasping point of the clip to grasp the wire-like material of the floss-wire component.

3. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 2 wherein the anchoring point of the clip protrudes outward toward the front of the clip.

4. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 3 wherein the anchoring point is defined by an aperture for receiving the floss-wire component.

5. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 4 wherein the end portion of the wire-like material is crimped, thereby preventing the wire-like material from completely passing through the anchoring point.

6. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 5 wherein the floss-like material of the floss-wire component is a flexible elongated strip of material having adequate strength when wet to resist breaking when pulled back and forth in an interproximal space between the teeth and sufficiently soft when wet to avoid pierce gum tissue.

7. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 5 wherein the floss-like material of the floss-wire component is multifilament floss.

8. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 5 wherein the wire-like material of the floss-wire component is 316L stainless steal.

9. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 5 wherein the wire-like material of the floss-wire component is polymer.

10. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 5 wherein the wire-like material of the floss-wire component is multifilament material.

11. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 5 wherein the clip includes a channel to provide a pathway for the wire-floss component.

12. The apparatus for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 1 further comprising a finger protruding from the clip wherein the finger receives the wire-like material from the grasping point whereby the crimping of the finger locks the wire-like material inside the finger, thereby preventing the wire-like material from retreating out of the grasping point.

13. A method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures, the method comprising the nonsequential steps of:
- inserting the floss-like material of a floss-wire component into the anchoring point of a clip;
- crimping the end portion of the wire-like material of a floss-wire component to prevent the end portion from passing through the anchoring point; and
- inserting the floss-like material of a floss-wire component into the grasping point of a clip until the floss-like material protrudes from the finger of the clip.

14. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 13 further comprising the step of engaging a clip with a bar.

15. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 14 further comprising the sequential steps of:
- flossing the floss-like material of the floss-wire component in the interproximal space of a first side of a tooth;
- directing the floss-like material around the lingual side of a tooth; and
- flossing the floss-like material of the floss-wire component in the interproximal space of a second side of a tooth.

16. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 15 further comprising the sequential step of pulling the floss-like material until the wire-like material substantially circumvents the tooth and protrudes from the finger of the clip.

17. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 16 further comprising the sequential step of continue pulling the floss-like material until the wire-like material is tightly secure around a tooth.

18. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 13 further comprising the sequential steps of:
- flossing the floss-like material of the floss-wire component in the interproximal space of a first side of a tooth;
- directing the floss-like material around the lingual side of a tooth; and
- flossing the floss-like material of the floss-wire component in the interproximal space of a second side of a tooth.

19. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 18 further comprising the sequential step of pulling the floss-like material until the wire-like material substantially circumvents the tooth and protrudes from a finger of the clip.

20. The method for supporting a maxillo-mandibular fixation of the maxillofacial region by securing the maxillary teeth and mandibular teeth together in a faster and less harmful manner, thereby stabilizing the bones of the jaws to effectuate proper healing of facial fractures of claim 19 further comprising the sequential step of continue pulling the floss-like material until the wire-like material is substantially secure around the tooth.

\* \* \* \* \*